(12) United States Patent
Wdowin

(10) Patent No.: US 10,610,495 B2
(45) Date of Patent: Apr. 7, 2020

(54) COMPOSITIONS FOR MITIGATING BRAIN TRAUMA AND METHODS THEREOF

(71) Applicant: Garrett E. Wdowin, Corona Del Mar, CA (US)

(72) Inventor: Garrett E. Wdowin, Corona Del Mar, CA (US)

( * ) Notice: Subject to any disclaimer, the term of this patent is extended or adjusted under 35 U.S.C. 154(b) by 0 days.

(21) Appl. No.: 16/666,224

(22) Filed: Oct. 28, 2019

(65) Prior Publication Data

US 2020/0060990 A1    Feb. 27, 2020

Related U.S. Application Data

(63) Continuation of application No. 16/030,546, filed on Jul. 9, 2018, now Pat. No. 10,456,368, which is a continuation-in-part of application No. 15/917,984, filed on Mar. 12, 2018, now abandoned, which is a continuation-in-part of application No. 15/878,288, filed on Jan. 23, 2018, now abandoned, which is a continuation-in-part of application No. 15/276,554, filed on Sep. 26, 2016, now abandoned.

(51) Int. Cl.

| | |
|---|---|
| *A61K 31/05* | (2006.01) |
| *A61K 31/7072* | (2006.01) |
| *A61P 25/00* | (2006.01) |
| *A61K 31/12* | (2006.01) |
| *A61K 31/661* | (2006.01) |
| *A61K 31/202* | (2006.01) |
| *A61K 9/107* | (2006.01) |
| *A61K 9/00* | (2006.01) |

(52) U.S. Cl.
CPC .............. *A61K 31/05* (2013.01); *A61K 9/009* (2013.01); *A61K 9/107* (2013.01); *A61K 31/12* (2013.01); *A61K 31/202* (2013.01); *A61K 31/661* (2013.01); *A61K 31/7072* (2013.01); *A61P 25/00* (2018.01); *A61K 9/0056* (2013.01)

(58) Field of Classification Search
None
See application file for complete search history.

(56) References Cited

U.S. PATENT DOCUMENTS 8,846,061 B1 *  9/2014  Bezzek ................ A61K 31/122
                                                 424/400

* cited by examiner

*Primary Examiner* — Nannette Holloman
(74) *Attorney, Agent, or Firm* — Rutan & Tucker LLP

(57) ABSTRACT

Disclosed herein is a formulation for mitigating brain trauma including, in some embodiments, one or more ω-3 fatty acids, one or more curcuminoids, trans-resveratrol, α-glycerylphosphorylcholine ("α-GPC"), and uridine-5'-monophosphate ("UMP"). The formulation is an oil-based emulsion including the one or more ω-3 fatty acids, the one or more curcuminoids, the trans-resveratrol, the α-GPC, and the UMP for oral administration. Also disclosed herein is a packaged formulation for mitigating brain trauma including, in some embodiments, a sealed pouch containing a single dose of the oil-based emulsion including the one or more ω-3 fatty acids, the one or more curcuminoids, trans-resveratrol, α-GPC, and UMP. Also disclosed herein is a method for mitigating brain trauma including, in some embodiments, administering the formulation before participating in an activity having an increased incidence of brain trauma, after participating in an activity having an increased incidence of brain trauma, or after sustaining brain trauma.

17 Claims, 1 Drawing Sheet

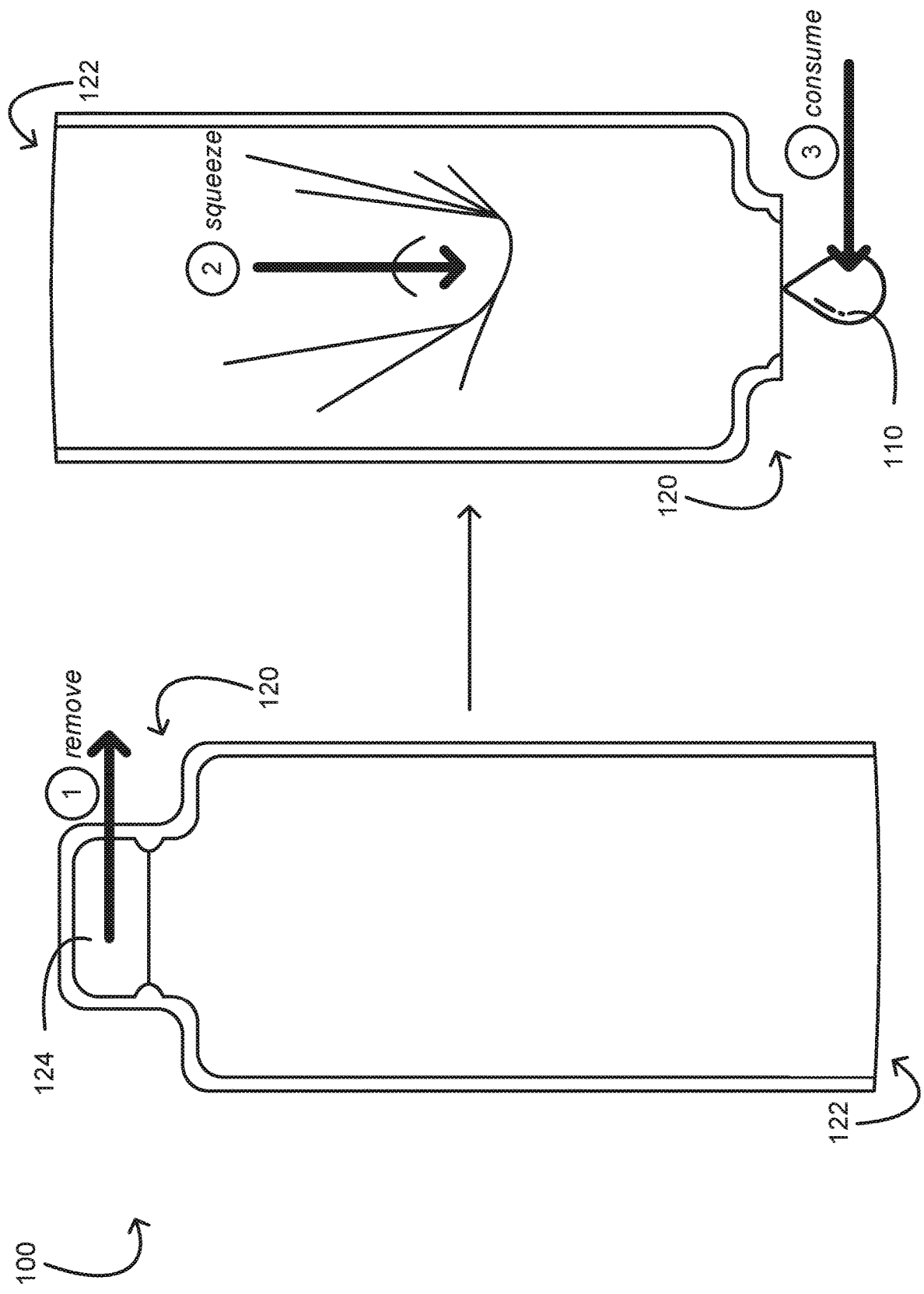

COMPOSITIONS FOR MITIGATING BRAIN TRAUMA AND METHODS THEREOF

PRIORITY

This application is a continuation of U.S. patent application Ser. No. 16/030,546, filed Jul. 9, 2018, now U.S. Pat. No. 10,456,368, which is a continuation-in-part of: 1) U.S. patent application Ser. No. 15/917,984, filed Mar. 12, 2018; 2) U.S. patent application Ser. No. 15/878,288 filed Jan. 23, 2018; and 3) U.S. patent application Ser. No. 15/276,554, filed Sep. 26, 2016. Each of the aforementioned applications is incorporated by reference in its entirety into this application.

BACKGROUND

A traumatic brain injury ("TBI") occurs when an external mechanical force such as a violent blow or jolt to the head causes brain dysfunction. Certain types of events are known to be more likely to cause TBIs including falls, collisions, fights, abuse, sports, explosive blasts, or the like. A TBI from one or more of such events can result in bruising of the brain; torn tissues in the brain; nerve damage; blood vessel damage leading to bleeding in or around the brain; fluid buildup in the cerebral ventricles of the brain; or even death. Long-term complications of TBIs can include cognitive problems such as issues with problem-solving and organization skills, as well as social and behavioral problems.

A TBI can be mild, moderate, or severe with symptoms dependent upon the severity of the trauma. A mild TBI, or concussion, can cause an injured person to experience physical symptoms such as headache, loss of consciousness, or nausea. With a moderate or severe TBI, an injured person can experience seizures or fall into a coma or a vegetative state. The severity of a TBI can be influenced by one or more factors including what part of the head was directly impacted, whether the brain moved back and forth in the skull upon impact, whether cellular structures were torn as a result of a severe rotational or spinning jolt, whether an object penetrated the skull, whether bleeding in or around the brain occurred, or the like.

Current measures for preventing or mitigating TBIs include physical measures such as buckling a seatbelt while riding in an automobile, cleaning a spill to avoid slipping in the spill, and wearing proper protective equipment (e.g., helmets) when participating in sporting events. However, there is currently a lack of remedial measures for mitigating brain trauma. As such, provided herein are compositions for mitigating brain trauma and methods thereof.

SUMMARY

Disclosed herein is a formulation for mitigating brain trauma including, in some embodiments, one or more ω-3 fatty acids, one or more curcuminoids, trans-resveratrol, α-glycerylphosphorylcholine ("α-GPC"), and uridine-5′-monophosphate ("UMP"). The formulation is an oil-based emulsion including the one or more ω-3 fatty acids, the one or more curcuminoids, the trans-resveratrol, the α-GPC, and the UMP for oral administration.

In some embodiments, the one or more ω-3 fatty acids include eicosapentaenoic acid ("EPA") in a concentration of about 2.8% (w/w) and docosahexaenoic acid ("DHA") in a concentration of about 1.9% (w/w) in the formulation.

In some embodiments, the one or more curcuminoids have a collective concentration of about 1.6% (w/w) in the formulation.

In some embodiments, the one or more curcuminoids include curcumin, demethoxycurcumin, and bisdemethoxycurcumin. The curcumin has a concentration of at least about 75% (w/w) in the one or more curcuminoids.

In some embodiments, the trans-resveratrol has a concentration of about 1.3% (w/w) in the formulation.

In some embodiments, the α-GPC has a concentration of about 0.9% (w/w) in the formulation.

In some embodiments, the UMP has a concentration of about 0.6% (w/w) in the formulation.

In some embodiments, the formulation further includes one or more emulsifiers, stabilizers, or thickeners selected from glycerin, gum arabic, xanthan gum, and guar gum.

In some embodiments, the formulation further includes xylitol, fish oil, natural flavors, ascorbic acid, monk fruit extract, citric acid, antioxidant blend, beta carotene, and sorbic acid.

In some embodiments, the formulation further includes one or more emulsifiers, stabilizers, or thickeners selected from glycerin, gum arabic, xanthan gum, and guar gum. The one or more ω-3 fatty acids include EPA in a concentration of about 2.8% (w/w) and DHA in a concentration of about 1.9% (w/w) in the formulation. The one or more curcuminoids include curcumin, demethoxycurcumin, and bisdemethoxycurcumin in a collective concentration of about 1.6% (w/w) in the formulation. The trans-resveratrol has a concentration of about 1.3% (w/w) in the formulation. The α-GPC has a concentration of about 0.9% (w/w) in the formulation. The UMP has a concentration of about 0.6% (w/w) in the formulation.

Also disclosed herein is a packaged formulation for mitigating brain trauma including, in some embodiments, an oil-based emulsion and a sealed pouch containing a single dose of the emulsion. The emulsion includes one or more ω-3 fatty acids, one or more curcuminoids, trans-resveratrol, α-GPC, and UMP.

In some embodiments, the pouch includes a bottom gusset configured to provide an inner space near a bottom of the pouch to contain the emulsion.

In some embodiments, the pouch includes a removable top piece of a top portion of the pouch configured to be torn off the pouch for access to the emulsion.

In some embodiments, the pouch includes a front side and a back side of a flexible material configured for squeezing the front and back sides of the pouch together to dispense the emulsion.

In some embodiments, the single dose of the emulsion is about 31.8 g including about 900 mg of EPA and about 600 mg of DHA for the one or more ω-3 fatty acids, about 500 mg of the one or more curcuminoids including at least curcumin, demethoxycurcumin, and bisdemethoxycurcumin, about 400 mg of the trans-resveratrol, about 300 mg of the α-GPC, and about 200 mg of the UMP. The pouch includes a bottom gusset configured to provide an inner space near a bottom of the pouch to contain the emulsion. The pouch includes a removable top piece of a top portion of the pouch configured to be torn off the pouch for access to the emulsion. The pouch includes a front side and a back side of a flexible material configured for squeezing the front and back sides of the pouch together to dispense the emulsion for oral administration.

Also disclosed is a method for mitigating brain trauma including, in some embodiments, obtaining a sealed pouch containing a formulation for mitigating brain trauma and administering the formulation per os to mitigate brain trauma. The formulation is an oil-based emulsion including one or more ω-3 fatty acids, one or more curcuminoids, trans-resveratrol, α-GPC, and UMP for oral administration.

In some embodiments, administering the formulation occurs before participating in an activity having an increased incidence of brain trauma.

In some embodiments, administering the formulation occurs after sustaining brain trauma or participating in an activity having an increased incidence of brain trauma.

In some embodiments, the method further includes tearing off a removable top piece of a top portion of the pouch and squeezing a front side and a back side of the pouch together in a motion from a bottom portion of the pouch to the top portion of the pouch to dispense the formulation from the pouch.

In some embodiments, the method further includes tearing off a removable top piece of a top portion of the pouch and squeezing a front side and a back side of the pouch together in a motion from a bottom portion of the pouch to the top portion of the pouch to dispense the formulation from the pouch. The pouch includes a single dose of the formulation for mitigating brain trauma including about 900 mg of EPA and about 600 mg of DHA for the one or more ω-3 fatty acids, about 500 mg of the one or more curcuminoids including at least curcumin, demethoxycurcumin, and bisdemethoxycurcumin, about 400 mg of the trans-resveratrol, about 300 mg of the α-GPC, and about 200 mg of the UMP.

These and other features of the concepts provided herein will become more apparent to those of skill in the art in view of the accompanying drawings and following description, which disclose particular embodiments of such concepts in greater detail.

DRAWINGS

FIG. 1 illustrates a packaged formulation for mitigating brain trauma in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "front," "back," "top," "bottom," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

"About," as in about a particular amount, concentration, or the like of a component in the composition or formulation for mitigating head trauma, is intended to reflect the particular amount or concentration of the component in the composition or formulation is within rounding or measurement uncertainty as it is defined in metrology. For example, a single dose of the formulation described herein for mitigating head trauma can be "about 31.8 g," which can include 31.79 g to 31.81 g of the formulation due to at least rounding.

"Oil-based," as in an "oil-based emulsion," indicates the oil-based emulsion has a dispersed phase of an oil (e.g., fish oil) and a continuous phase of an immiscible liquid such as water.

Abbreviations, initialisms, acronyms, or the like used herein include eicosapentaenoic acid ("EPA"), docosahexaenoic acid ("DHA"), α-glycerylphosphorylcholine ("α-GPC"), parts per million by weight ("ppmw"), traumatic brain injury ("TBI"), and uridine-5'-monophosphate ("UMP"). Other abbreviations, initialisms, acronyms, or the like are provided herein upon usage.

Unless defined otherwise, all technical and scientific terms used herein have the same meaning as commonly understood by those of ordinary skill in the art.

Again, current measures for preventing or mitigating TBIs include physical measures. However, there is currently a lack of remedial measures for mitigating brain trauma. As such, provided herein are compositions for mitigating brain trauma and methods thereof.

Compositions and Formulations Thereof

A composition for mitigating brain trauma includes, in some embodiments, one or more ω-3 fatty acids, one or more curcuminoids, and trans-resveratrol. Optionally, the composition can further include α-GPC, UMP, or both α-GPC and UMP. The composition mitigates brain trauma by providing brain health in the form of neuroprotective support including axonal protection. The composition also supports cognition, memory, and concentration.

The composition for mitigating brain trauma can be formulated into any administrable formulation that provides sufficient plasma levels of the compounds (e.g., EPA, DHA, curcumin, and trans-resveratrol) in the composition to mitigate brain trauma upon administration of one or more doses of the formulation. In addition to the composition, the formulation can include any nutraceutically acceptable excipients needed for a multidose or single-dose dosage form suitable for at least enteral administration such as oral, lingual, sublingual, or buccal administration. The multidose dosage form can be a bulk powder, paste, suspension, emulsion, or solution including the composition. The single-dose dosage form can be a pre-measured amount of the powder; a pill, tablet, or capsule including effervescent, chewable, and orally disintegrating forms thereof; a pre-cut, orally disintegrating thin film; a pre-measured amount of the paste; or a pre-measured amount of the suspension, emulsion, or solution. For example, the composition can be formulated into an oil-based emulsion for oral administration, which emulsion can be pre-measured and packaged in a pouch as a single dose. (See FIG. 1.) Oral administration is advantageous due to its convenience and ease of implementation.

With respect to dosage, a single dose of the formulation including the composition for mitigating brain trauma can include at least about 10 g, 20 g, 30 g, 40 g, 50 g, 60 g, 70 g, 80 g, 90 g, or 100 g, or an intervening amount (e.g., 31 g, 32 g, 33 g, 34 g, of 35 g), of the formulation for an average sized man or woman. Alternatively, a single dose of the formulation including the composition for mitigating brain trauma can include no more than about 100 g, 90 g, 80 g, 70 g, 60 g, 50 g, 40 g, 30 g, 20 g, or 10 g, or an intervening amount (e.g., 35 g, 34 g, 33 g, 32 g, of 31 g), of the formulation. As such, a single dose of the formulation including the composition for mitigating brain trauma can include at least about 10 g and no more than about 100 g of the formulation, which includes at least about 20 g and no more than about 70 g of the formulation, such as at least about 30 g and no more than about 40 g of the formulation, for example, at least about 30 g and no more than about 35 g of the formulation. In some embodiments, a single dose of the formulation including the composition for mitigating brain trauma is 31.8 g (30 mL) of the formulation.

Omega-3 Fatty Acids

The one or more ω-3 fatty acids in the composition for mitigating brain trauma can include, but are not limited to, EPA and DHA. For example, the ω-3 fatty acids can further include hexadecatrienoic acid ("HTA"), α-linolenic acid ("ALA"), stearidonic acid ("SDA"), eicosatrienoic acid ("ETE"), eicosatetraenoic acid ("ETA"), heneicosapentaenoic acid ("HPA"), docosapentaenoic acid ("DPA"), tetracosapentaenoic acid, or tetracosahexaenoic acid (nisinic acid), structural analogs including isomers such as geometric isomers of the foregoing, oligomers such as dimers of the foregoing, or chemical derivatives, salts, hydrates, or solvates of the foregoing. ALA is important in some embodiments as each ω-3 fatty acid of EPA and DHA can be biosynthesized from ALA. The efficiency of such a conversion can be relatively low, which is why EPA and DHA are included in at least some embodiments of the composition for mitigating brain trauma.

Both EPA and DHA are precursors to resolvins and protectins, which orchestrate inflammation recovery. Numerous body functions are attributed to at least DHA including neuronal processes such as neurogenesis, neuroplasticity, neurite outgrowth, synaptogenesis, and membrane fluidity. Indeed, administration of long-chain ω-3 fatty acids such as EPA and DHA has been found to promote neurogenesis and exert a neurotrophic effect. DHA increases cerebral blood flow and regulates glucose transport and uptake. DHA also affects biomarkers such as plasma fatty acids and serum neurofilament light ("NfL"), a biomarker of trauma. DHA has been shown to attenuate damage to axons when ingested before an injury. Indeed, it has been found a rich concentration of DHA is associated with a reduced number of injured axons in vulnerable populations. Therefore, ω-3 fatty acids such as EPA and DHA provide a neuroprotective effect, as it relates to axonal injury, which is known as the central mechanism in mild TBI.

With respect to the EPA in the formulation, the formulation can include at least about 0.5% (w/w), 1.0% (w/w), 1.5% (w/w), 2.0% (w/w), 2.5% (w/w), 3.0% (w/w), 3.5% (w/w), 4.0% (w/w), 4.5% (w/w), or 5.0% (w/w) EPA, or an intervening concentration (e.g., 2.6% (w/w), 2.7% (w/w), 2.8% (w/w), or 2.9% (w/w) EPA) thereof, in the formulation. Alternatively, the formulation can include no more than about 5.0% (w/w), 4.5% (w/w), 4.0% (w/w), 3.5% (w/w), 3.0% (w/w), 2.5% (w/w), 2.0% (w/w), 1.5% (w/w), 1.0% (w/w), or 0.5% (w/w) EPA, or an intervening concentration (e.g., 2.9% (w/w), 2.8% (w/w), 2.7% (w/w), or 2.6% (w/w) EPA) thereof, in the formulation. As such, the formulation can include EPA in a concentration range of at least about 0.5% (w/w) and no more than about 5.0% (w/w) EPA, which includes at least about 1.0% (w/w) and no more than about 4.0% (w/w) EPA, such as at least about 1.5% (w/w) and no more than about 3.0% (w/w) EPA, for example, at least about 2.5% (w/w) and no more than about 3.0% (w/w) EPA in the formulation. In some embodiments, for example, the formulation includes about 2.8% (w/w) EPA in the formulation. Depending upon the mechanism by which the EPA combined with, for example, the DHA, the one or more curcuminoids, the trans-resveratrol, the α-GPC, or the UMP, produces the synergistic effect of the formulation for mitigating brain trauma, the concentration of the EPA can be increased or reduced in the formulation as needed for optimization of the synergistic effect. (See Jia, Jia, et al. "Mechanisms of drug combinations: interaction and network perspectives." Nature reviews Drug discovery 8.2 (2009): 111.)

With respect to the DHA in the formulation, the formulation can include at least about 0.5% (w/w), 1.0% (w/w), 1.5% (w/w), 2.0% (w/w), 2.5% (w/w), 3.0% (w/w), 3.5% (w/w), 4.0% (w/w), 4.5% (w/w), or 5.0% (w/w) DHA, or an intervening concentration (e.g., 1.6% (w/w), 1.7% (w/w), 1.8% (w/w), or 1.9% (w/w) DHA) thereof, in the formulation. Alternatively, the formulation can include no more than about 5.0% (w/w), 4.5% (w/w), 4.0% (w/w), 3.5% (w/w), 3.0% (w/w), 2.5% (w/w), 2.0% (w/w), 1.5% (w/w), 1.0% (w/w), or 0.5% (w/w) DHA, or an intervening concentration (e.g., 1.9% (w/w), 1.8% (w/w), 1.7% (w/w), or 1.6% (w/w) DHA) thereof, in the formulation. As such, the formulation can include DHA in a concentration range of at least about 0.5% (w/w) and no more than about 5.0% (w/w) DHA, which includes at least about 1.0% (w/w) and no more than about 4.0% (w/w) DHA, such as at least about 1.5% (w/w) and no more than about 3.0% (w/w) DHA, for example, at least about 1.5% (w/w) and no more than about 2.0% (w/w) DHA in the formulation. In some embodiments, for example, the formulation includes about 1.9% (w/w) DHA in the formulation. Depending upon the mechanism by which the DHA combined with, for example, the EPA, the one or more curcuminoids, the trans-resveratrol, the α-GPC, or the UMP, produces the synergistic effect of the formulation for mitigating brain trauma, the concentration of the DHA can be increased or reduced in the formulation as needed for optimization of the synergistic effect.

Curcuminoids

The one or more curcuminoids in the composition for mitigating brain trauma can include, but are not limited to, curcumin, demethoxycurcumin, and, optionally, bisdemethoxycurcumin. For example, the one or more curcuminoids can further include additional structural analogs of curcumin other than demethoxycurcumin and bisdemethoxycurcumin including isomers such as geometric isomers, oligomers such as dimers, or chemical derivatives, salts, hydrates, or solvates of the foregoing. With respect to at least the curcumin, demethoxycurcumin, and, bisdemethoxycurcumin, the curcumin can have a concentration of at least about 75% (w/w) in the one or more curcuminoids, the demethoxycurcumin can have a concentration of at least about 15% (w/w) in the one or more curcuminoids, and, when present, the bisdemethoxycurcumin can have a concentration of at least about 2.5% (w/w) in the one or more curcuminoids. The one or more curcuminoids can be extracted from turmeric root (e.g., *Curcuma longa* or *Curcuma zedoaria*), which is known to contain up to at least 95% curcuminoids.

Polyphenols such as curcumin, demethoxycurcumin, and bisdemethoxycurcumin combat oxidative stress associated with neurons, thereby providing neuroprotective benefits. Mechanisms associated with such neuroprotection include reducing monocyte chemoattractant protein 1 ("MCP1") production as shown in different cell lines. Additionally, such polyphenols decrease messenger ribonucleic acid ("mRNA") expression of MCP1, interleukin 1-β, and interleukin-6, as well as ameliorate enhanced expression of ionized calcium binding in the hippocampus. Polyphenols such as curcumin, demethoxycurcumin, and bisdemethoxycurcumin also ameliorate the effects of chronic stress through reduction of cyclooxygenase-2 ("COX-2") levels, thereby contributing antioxidant potential and neuroprotective effects by way of free-radical scavenging. At least curcumin has been shown to increase serum activities of antioxidants (e.g., superoxide dismutase ["SOD"]) and modulate glutathione ("GSH"), catalase, and SOD activity. Polyphenols such as curcumin, demethoxycurcumin, and bisdemethoxycurcumin also improve cognitive function including memory as evidenced by recall tests, picture-recognition tests, and various recall evaluations. In one example, the intake of curcumin among other curcuminoids within a predetermined time period prior to brain trauma reduces cerebral edema, which can develop as a result of inflammation caused by TBI.

With respect to the one or more curcuminoids in the formulation, the formulation can collectively include at least about 0.5% (w/w), 1.0% (w/w), 1.5% (w/w), 2.0% (w/w), 2.5% (w/w), 3.0% (w/w), 3.5% (w/w), 4.0% (w/w), 4.5% (w/w), or 5.0% (w/w) of the one or more curcuminoids, or an intervening concentration (e.g., 1.6% (w/w), 1.7% (w/w), 1.8% (w/w), or 1.9% (w/w) of the one or more curcuminoids) thereof, in the formulation. Alternatively, the formulation can include no more than about 5.0% (w/w), 4.5% (w/w), 4.0% (w/w), 3.5% (w/w), 3.0% (w/w), 2.5% (w/w), 2.0% (w/w), 1.5% (w/w), 1.0% (w/w), or 0.5% (w/w) of the one or more curcuminoids, or an intervening concentration (e.g., 1.9% (w/w), 1.8% (w/w), 1.7% (w/w), or 1.6% (w/w) of the one or more curcuminoids) thereof, in the formulation. As such, the formulation can include the one or more curcuminoids in a concentration range of at least about 0.5% (w/w) and no more than about 5.0% (w/w) of the one or more curcuminoids, which includes at least about 1.0% (w/w) and no more than about 4.0% (w/w) of the one or more curcuminoids, such as at least about 1.0% (w/w) and no more than about 3.0% (w/w) of the one or more curcuminoids, for example, at least about 1.0% (w/w) and no more than about 2.0% (w/w) of the one or more curcuminoids in the formulation. In some embodiments, for example, the formulation includes about 1.6% (w/w) of the one or more curcuminoids in the formulation. Depending upon the mechanism by which the one or more curcuminoids combined with, for example, the EPA, the DHA, the trans-resveratrol, the α-GPC, or the UMP, produces the synergistic effect of the formulation for mitigating brain trauma, the concentration of the one or more curcuminoids can be increased or reduced in the formulation as needed for optimization of the synergistic effect.

Resveratrol

The resveratrol in the composition for mitigating brain trauma can include, but is not limited to, trans-resveratrol. For example, the resveratrol can further include structural analogs of resveratrol including isomers such as geometric isomers (e.g., cis-resveratrol), oligomers of resveratrol such as dimers (e.g., restrytisol A, B, or C; resveratrol trans-dehydrodimer; leachinol F; or pallidol), or chemical derivatives (e.g., resveratrol 3-O-beta-D-glucoside), salts, hydrates, or solvates of the foregoing.

Trans-resveratrol improves memory performance and hippocampal function. Indeed, daily intake of trans-resveratrol has shown increases in hippocampal functional connectivity associated with memory retention scores of patients ingesting the trans-resveratrol. Furthermore, proinflammatory cytokine concentration is reduced with trans-resveratrol, which is beneficial to reduce interleukin 1-β and tumor necrosis factor, each of which negatively impacts the central nervous system. In vivo and in vitro models have shown trans-resveratrol inhibits free radical formation and cyclooxygenase-1 ("COX-1") activity.

With respect to the trans-resveratrol in the formulation, the formulation can include at least about 0.5% (w/w), 1.0% (w/w), 1.5% (w/w), 2.0% (w/w), 2.5% (w/w), 3.0% (w/w), 3.5% (w/w), 4.0% (w/w), 4.5% (w/w), or 5.0% (w/w) trans-resveratrol, or an intervening concentration (e.g., 1.1% (w/w), 1.2% (w/w), 1.3% (w/w), or 1.4% (w/w) trans-resveratrol) thereof, in the formulation. Alternatively, the formulation can include no more than about 5.0% (w/w), 4.5% (w/w), 4.0% (w/w), 3.5% (w/w), 3.0% (w/w), 2.5% (w/w), 2.0% (w/w), 1.5% (w/w), 1.0% (w/w), or 0.5% (w/w) trans-resveratrol, or an intervening concentration (e.g., 1.4% (w/w), 1.3% (w/w), 1.2% (w/w), or 1.1% (w/w) trans-resveratrol) thereof, in the formulation. As such, the formulation can include trans-resveratrol in a concentration range of at least about 0.5% (w/w) and no more than about 5.0% (w/w) trans-resveratrol, which includes at least about 1.0% (w/w) and no more than about 4.0% (w/w) trans-resveratrol, such as at least about 1.0% (w/w) and no more than about 3.0% (w/w) trans-resveratrol, for example, at least about 1.0% (w/w) and no more than about 2.0% (w/w) trans-resveratrol in the formulation. In some embodiments, for example, the formulation includes about 1.3% (w/w) trans-resveratrol in the formulation. Depending upon the mechanism by which the trans-resveratrol combined with, for example, the EPA, the DHA, the one or more curcuminoids, the α-GPC, or the UMP, produces the synergistic effect of the formulation for mitigating brain trauma, the concentration of the trans-resveratrol can be increased or reduced in the formulation as needed for optimization of the synergistic effect.

α-glycerylphosphorylcholine

With respect to the α-GPC in the formulation, the formulation can include at least about 0.5% (w/w), 1.0% (w/w), 1.5% (w/w), 2.0% (w/w), 2.5% (w/w), 3.0% (w/w), 3.5% (w/w), 4.0% (w/w), 4.5% (w/w), or 5.0% (w/w) α-GPC, or an intervening concentration (e.g., 0.6% (w/w), 0.7% (w/w), 0.8% (w/w), or 0.9% (w/w) α-GPC) thereof, in the formulation. Alternatively, the formulation can include no more than about 5.0% (w/w), 4.5% (w/w), 4.0% (w/w), 3.5% (w/w), 3.0% (w/w), 2.5% (w/w), 2.0% (w/w), 1.5% (w/w), 1.0% (w/w), or 0.5% (w/w) α-GPC, or an intervening concentration (e.g., 0.9% (w/w), 0.8% (w/w), 0.7% (w/w), or 0.6% (w/w) α-GPC) thereof, in the formulation. As such, the formulation can include α-GPC in a concentration range of at least about 0.5% (w/w) and no more than about 5.0% (w/w) α-GPC, which includes at least about 0.5% (w/w) and no more than about 3.5% (w/w) α-GPC, such as at least about 0.5% (w/w) and no more than about 2.0% (w/w) α-GPC, for example, at least about 0.5% (w/w) and no more than about 1.0% (w/w) α-GPC in the formulation. In some embodiments, for example, the formulation includes about 0.9% (w/w) α-GPC in the formulation. Depending upon the mechanism by which the α-GPC combined with, for example, the EPA, the DHA, the one or more curcuminoids, the trans-resveratrol, or the UMP, produces the synergistic effect of the formulation for mitigating brain trauma, the concentration of the α-GPC can be increased or reduced in the formulation as needed for optimization of the synergistic effect.

Uridine-5'-Monophosphate

UMP provides bioavailable uridine, which, together with at least the DHA, enhances learning and memory.

With respect to the UMP in the formulation, the formulation can include at least about 0.5% (w/w), 1.0% (w/w), 1.5% (w/w), 2.0% (w/w), 2.5% (w/w), 3.0% (w/w), 3.5% (w/w), 4.0% (w/w), 4.5% (w/w), or 5.0% (w/w) UMP, or an intervening concentration (e.g., 0.6% (w/w), 0.7% (w/w), 0.8% (w/w), or 0.9% (w/w) UMP) thereof, in the formulation. Alternatively, the formulation can include no more than about 5.0% (w/w), 4.5% (w/w), 4.0% (w/w), 3.5% (w/w), 3.0% (w/w), 2.5% (w/w), 2.0% (w/w), 1.5% (w/w), 1.0% (w/w), or 0.5% (w/w) UMP, or an intervening concentration (e.g., 0.9% (w/w), 0.8% (w/w), 0.7% (w/w), or 0.6% (w/w) UMP) thereof, in the formulation. As such, the formulation can include UMP in a concentration range of at least about 0.5% (w/w) and no more than about 5.0% (w/w) UMP, which includes at least about 0.5% (w/w) and no more than about 3.5% (w/w) UMP, such as at least about 0.5% (w/w) and no more than about 2.0% (w/w) UMP, for example, at least about 0.5% (w/w) and no more than about 1.0% (w/w) UMP in the formulation. In some embodiments, for example, the formulation includes about 0.6% (w/w) UMP in the formulation. Depending upon the mechanism by which the UMP combined with, for example, the EPA, the DHA, the one or more curcuminoids, the trans-resveratrol, or the α-GPC, produces the synergistic effect of the formulation for mitigating brain trauma, the concentration of the UMP can be increased or reduced in the formulation as needed for optimization of the synergistic effect.

Nutraceutically Acceptable Excipients

As set forth above, the formulation including the composition for mitigating head trauma can include any nutraceutically acceptable excipients needed for a multidose or single-dose dosage form suitable for at least enteral administration. Such excipients include, but are not limited to, antiadherents, binders, coatings, colors, disintegrants, emulsifiers, flavors, glidants, lubricants, preservatives, sorbents, stabilizers, sweeteners, thickeners, vehicles, or combinations thereof.

When the composition is formulated into an oil-based emulsion for oral administration, the formulation can further include one or more emulsifiers, stabilizers, or thickeners selected from at least glycerin, gum arabic, xanthan gum, and guar gum. An emulsifier, stabilizer, or thickener such as glycerin, gum arabic, xanthan gum, or guar gum can fulfill more than one role in an emulsion. For example, when the composition is formulated into the oil-based emulsion with each of glycerin, gum arabic, xanthan gum, and guar gum, the glycerin can act as a thickener, the gum arabic can act as an emulsifier, stabilizer, or thickener, the xanthan gum can act as stabilizer or thickener, and the guar gum can act as an emulsifier, stabilizer, or thickener.

In addition to the emulsifiers, stabilizers, or thickeners, selected from glycerin, gum arabic, xanthan gum, and guar gum, the formulation including the composition for mitigating head trauma can also include xylitol, fish oil (e.g., fish oil derived from anchovy, sardine, or mackerel), natural flavors, ascorbic acid, monk fruit extract, citric acid, an antioxidant blend (e.g., vitamin E as α-tocopherol, rosemary extract, and ascorbyl palmitate), beta carotene (for color), and sorbic acid.

With respect to the ascorbic acid, or vitamin C, in the formulation, the formulation can include at least about 0.5% (w/w), 1.0% (w/w), 1.5% (w/w), 2.0% (w/w), 2.5% (w/w), 3.0% (w/w), 3.5% (w/w), 4.0% (w/w), 4.5% (w/w), or 5.0% (w/w) vitamin C, or an intervening concentration (e.g., 0.6% (w/w), 0.7% (w/w), 0.8% (w/w), or 0.9% (w/w) vitamin C) thereof, in the formulation. Alternatively, the formulation can include no more than about 5.0% (w/w), 4.5% (w/w), 4.0% (w/w), 3.5% (w/w), 3.0% (w/w), 2.5% (w/w), 2.0% (w/w), 1.5% (w/w), 1.0% (w/w), or 0.5% (w/w) vitamin C, or an intervening concentration (e.g., 0.9% (w/w), 0.8% (w/w), 0.7% (w/w), or 0.6% (w/w) vitamin C) thereof, in the formulation. As such, the formulation can include vitamin C in a concentration range of at least about 0.5% (w/w) and no more than about 5.0% (w/w) vitamin C, which includes at least about 0.5% (w/w) and no more than about 3.5% (w/w) vitamin C, such as at least about 0.5% (w/w) and no more than about 2.0% (w/w) vitamin C, for example, at least about 0.5% (w/w) and no more than about 1.0% (w/w) vitamin C in the formulation. In some embodiments, for example, the formulation includes about 0.6% (w/w) vitamin C in the formulation.

With respect to the vitamin E in the formulation, the formulation can include at least about 150 ppmw, 300 ppmw, 450 ppmw, 600 ppmw, 750 ppmw, or 900 ppmw, or an intervening concentration (e.g., 315 ppmw, 330 ppmw, 345 ppmw, 360 ppmw, 375 ppmw, 390 ppmw, 405 ppmw, 420 ppmw, 435 ppmw, or 450 ppmw vitamin E) thereof, in the formulation. Alternatively, the formulation can include no more than about 900 ppmw, 750 ppmw, 600 ppmw, 450 ppmw, 300 ppmw, or 150 ppmw vitamin E, or an intervening concentration (e.g., 450 ppmw, 435 ppmw, 420 ppmw, 405 ppmw, 390 ppmw, 375 ppmw, 360 ppmw, 345 ppmw, 330 ppmw, or 315 ppmw vitamin E) thereof, in the formulation. As such, the formulation can include vitamin E in a concentration range of at least about 150 ppmw and no more than about 900 ppmw vitamin E, which includes at least about 150 ppmw and no more than about 750 ppmw vitamin E, such as at least about 150 ppmw and no more than about 600 ppmw vitamin E, for example, at least about 150 ppmw and no more than about 450 ppmw vitamin E in the formulation. In some embodiments, for example, the formulation includes about 315 ppmw vitamin E in the formulation.

In view of the foregoing, the formulation can be an emulsion including one or more ω-3 fatty acids including EPA in a concentration of about 2.8% (w/w) and DHA in a concentration of about 1.9% (w/w); one or more curcuminoids including curcumin, demethoxycurcumin, and, optionally, bisdemethoxycurcumin in a collective concentration of about 1.6% (w/w); trans-resveratrol in a concentration of about 1.3% (w/w); α-GPC in a concentration of about 0.9% (w/w); and UMP in a concentration of about 0.6% (w/w) formulated for oral administration in about a 31.8-g (30-mL) dose. The can further include xylitol, fish oil, glycerin, gum arabic, natural flavors, ascorbic acid, monk fruit extract, xanthan gum, citric acid, guar gum, an antioxidant blend (e.g., vitamin E as α-tocopherol, rosemary extract, and ascorbyl palmitate), beta carotene, and sorbic acid.

As set forth above, a single dose of the formulation for mitigating brain trauma can range from at least about 10 g and no more than about 100 g of the formulation, which range also includes intervening amounts of the formulation, for example, 31.8 g (30 mL) of the formulation. In addition, various concentrations are set forth herein for the compounds in the formulation. For example, the formulation can include EPA in a concentration range of at least about 0.5% (w/w) and no more than about 5.0% (w/w) EPA (e.g., 2.8% (w/w) EPA); DHA in a concentration range of at least about 0.5% (w/w) and no more than about 5.0% (w/w) DHA (e.g., 2.0% (w/w) DHA); the one or more curcuminoids in a concentration range of at least about 0.5% (w/w) and no more than about 5.0% (w/w) of the one or more curcuminoids (e.g., 1.6% (w/w) of the one or more curcuminoids); trans-resveratrol in a concentration range of at least about 0.5% (w/w) and no more than about 5.0% (w/w) trans-resveratrol (e.g., 1.3% (w/w) trans-resveratrol); α-GPC in a concentration range of at least about 0.5% (w/w) α-GPC and no more than about 5.0% (w/w) α-GPC (e.g., 0.9% (w/w) α-GPC); and UMP in a concentration range of at least about 0.5% (w/w) UMP and no more than about 5.0% (w/w) UMP (e.g., 0.6% (w/w) UMP). Routine dimensional analysis for the foregoing example concentrations of the compounds in the example 31.8-g dose of the formulation provides about 900 mg of EPA, about 600 mg of DHA, about 500 mg of the one or more curcuminoids, about 400 mg of trans-resveratrol, about 300 mg of the α-GPC, and about 200 mg of UMP in the 31.8-g dose of the formulation. Such routine dimensional analysis for converting between concentrations and amounts is available in most general chemistry or analytical chemistry textbooks and is hereby incorporated herein by reference. As such, it should be understood that any compound or compounds (e.g., the one or more curcuminoids) having a concentration set forth herein also has an associated amount for any single dose of the formulation set forth herein. Such amounts are not enumerated in view of expository expediency. Furthermore, it should be understood that any two or more compounds having a concentration set forth herein also has an associated concentration-based ratio that can be routinely determined in accordance with basic mathematics. Such concentration-based ratios are not enumerated in view of expository expediency.

The EPA, the DHA, the one or more curcuminoids, the trans-resveratrol, the α-GPC, and the UMP of the formulation for mitigating brain trauma can be sourced from nature (e.g., a plant or animal extract) or synthesized.

Advantages of the formulation for mitigating brain trauma include providing nutritional building blocks and powerful antioxidants that increase cerebral blood flow, protect the brain from oxidative stress, and reduce neuroinflammation and post-traumatic loss of neurons following brain trauma, thereby lessening any acute damage associated with the brain trauma, especially concussion. Furthermore, the formulation for mitigating brain trauma can assist in the neurological repair needed following such brain trauma. Indeed, the formulation for mitigating brain trauma stimulates the repair of nerve cells damaged as a result of brain trauma. In particular, at least the DHA (along with other ω-3 fatty acids), trans-resveratrol, and curcumin, can stimulate repair of nerve cells damaged from brain trauma. Therefore, the formulation for mitigating brain trauma is useful for reducing the duration or severity of concussive symptoms and associated neurological damage from brain trauma.

Packaged Formulations

FIG. 1 illustrates a packaged formulation 100 for mitigating brain trauma in accordance with some embodiments.

The packaged formulation 100 for mitigating brain trauma includes, in some embodiments, an oil-based emulsion 110 as set forth herein and a pouch 120 containing a single dose of the emulsion 110 when the pouch 120 is initially sealed. The pouch 120 includes a bottom gusset 122 at a bottom portion of the pouch 120 configured to provide an inner space in the bottom portion of the pouch 120 to contain the emulsion 110. The pouch also 120 includes a removable top piece 124 of a top portion of the pouch 120. The removable top piece 124 is configured to be torn off the pouch 120 for access to the emulsion 110. The pouch 120 includes a front side and a back side of a same or different flexible construction. For example, each side of the front side and the back side can be a laminate of one or more layers of polyester, nylon, aluminum, polypropylene, or polyethylene. The polyester can provide a glossy, rigid layer that can be printed on, the nylon can provide puncture resistance, the aluminum can provide a thin, effective gas barrier, the polypropylene can be food-grade cast polypropylene, which can be used as a sealing layer, and the polyethylene can be used instead of polypropylene as the sealing layer, as well as a bonding layer. The pouch 120 is configured for squeezing the front side and the back side together to dispense the emulsion 110 from the pouch 120 once the removable top piece 124 is torn off the pouch 120.

The single dose of the emulsion 110 in the pouch 120 can be about 31.8 g (30 mL) including about 900 mg of EPA and about 600 mg of DHA for the one or more ω-3 fatty acids, about 500 mg of the one or more curcuminoids including at least curcumin, demethoxycurcumin, and, optionally, bisdemethoxycurcumin, and about 400 mg of the trans-resveratrol. Optionally, the emulsion 110 further includes about 300 mg of the α-GPC and about 200 mg of the UMP.

Methods

A method for mitigating brain trauma includes, in some embodiments, obtaining the pouch 120 containing a formulation sealed therein for mitigating brain trauma and administering the formulation per os to mitigate brain trauma. As set forth herein, the formulation can include a single dose of the oil-based emulsion 110 of one or more ω-3 fatty acids, one or more curcuminoids, and trans-resveratrol. Optionally, the emulsion 110 further includes α-GPC and about UMP.

The method further includes tearing off the removable top piece 124 of the top portion of the pouch 120 and squeezing the front side and the back side of the pouch 120 together in a motion from the bottom portion of the pouch 120 to the top portion of the pouch 120 to dispense the formulation from the pouch 120. Again, the formulation for mitigating brain trauma that is sealed in the pouch 120 can include a single dose of the emulsion 110. The emulsion 110 can include about 900 mg of EPA and about 600 mg of DHA for the one or more ω-3 fatty acids, about 500 mg of the one or more curcuminoids including at least curcumin, demethoxycurcumin, and, optionally, bisdemethoxycurcumin, and about 400 mg of the trans-resveratrol. Optionally, the emulsion 110 further includes about 300 mg of the α-GPC and about 200 mg of the UMP.

Administering the formulation to mitigate brain trauma can occur before participating in an activity having an increased incidence of brain trauma. Such an activity can include, but is not limited to, sports such as boxing, football, hockey, soccer, lacrosse, or wrestling, in which sports a concussion is possible. The formulation including the composition for mitigating brain trauma can be administered to an individual or self-administered by the individual a period of time up to about an hour before participating in the activity such as at least 5 minutes, 10 minutes, 15 minutes, 30 minutes, 45 minutes, or 60 minutes before participating in the activity. Alternatively, the formulation including the composition for mitigating brain trauma can be administered to an individual or self-administered by the individual a period of time no more than about an hour before participating in the activity such as no more than 60 minutes, 45 minutes, 30 minutes, 15 minutes, 10 minutes, or 5 minutes before participating in the activity. The formulation including the composition for mitigating brain trauma can be administered to the individual or self-administered by the individual a period of time up to about a day before participating in the activity such as at least 2 hours, 4 hours, 6 hours, 8 hours, 12 hours, 16 hours, 20 hours, or 24 hours before participating in the activity. The formulation including the composition for mitigating brain trauma can be administered to the individual or self-administered by the individual a period of time no more than about a day before participating in the activity such as at least 2 hours, 4 hours, 6 hours, 8 hours, 12 hours, 16 hours, 20 hours, or 24 hours before participating in the activity.

Administering the formulation to mitigate brain trauma can occur while participating in an activity having an increased incidence of brain trauma. Again, such an activity can include, but is not limited to, sports such as boxing, football, hockey, soccer, lacrosse, or wrestling, in which sports. The formulation including the composition for mitigating brain trauma can be administered to an individual or self-administered by the individual during a break in the activity such as between rounds of a boxing match, during halftime in a game of football, during intermission in a game of hockey, or the like.

Administering the formulation to mitigate brain trauma can occur after participating in an activity having an increased incidence of brain trauma or even after sustaining brain trauma. Again, such an activity can include, but is not limited to, sports such as boxing, football, hockey, soccer, lacrosse, or wrestling, in which sports a concussion is possible. The formulation including the composition for mitigating brain trauma can be administered to an individual or self-administered by the individual a period of time up to about an hour after participating in the activity or sustaining brain trauma such as at least 5 minutes, 10 minutes, 15 minutes, 30 minutes, 45 minutes, or 60 minutes after participating in the activity or sustaining brain trauma. Alternatively, the formulation including the composition for mitigating brain trauma can be administered to an individual or self-administered by the individual a period of time no more than about an hour after participating in the activity or sustaining brain trauma such as no more than 60 minutes, 45 minutes, 30 minutes, 15 minutes, 10 minutes, or 5 minutes after participating in the activity or sustaining brain trauma. The formulation including the composition for mitigating brain trauma can be administered to the individual or self-administered by the individual a period of time up to about a day after participating in the activity or sustaining brain trauma such as at least 2 hours, 4 hours, 6 hours, 8 hours, 12 hours, 16 hours, 20 hours, or 24 hours after participating in the activity or sustaining brain trauma. The formulation including the composition for mitigating brain trauma can be administered to the individual or self-administered by the individual a period of time no more than about a day after participating in the activity or sustaining brain trauma such as at least 2 hours, 4 hours, 6 hours, 8 hours, 12 hours, 16 hours, 20 hours, or 24 hours before participating in the activity or sustaining brain trauma.

Administering the formulation to mitigate brain trauma can occur a number of times a day before participating in an activity having an increased incidence of brain trauma, while participating in a same or different activity having an increased incidence of brain trauma, after participating in yet another same or different activity having an increased incidence of brain trauma, or a combination thereof. The number of times a day the formulation can be administered to mitigate brain trauma can include at least 1, 2, 3, 4, 5, 6, 7, 8, 9, or 10 times per day. Alternatively, the number of times a day the formulation can be administered to mitigate brain trauma can include no more than 10, 9, 8, 7, 6, 5, 4, 3, 2, or 1 time per day. As such, the number of times a day the formulation can be administered to mitigate brain trauma can include at least 1 time to no more than 10 times per day, which includes at least 1 time to no more than 8 times per day, such as at least about 1 time to no more than about 6 times per day, for example, at least about 1 time to no more than about 4 times per day. Each time of the number of times the formulation is administered can include administration of one or more single doses of the formulation, optionally, from one or more pouches such as the pouch 120.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures can be made from the particular embodiments disclosed herein without departing from the scope of the concepts provided herein.

What is claimed is:

1. A method for improving cognitive function, comprising:
   obtaining a formulation for improving cognitive function, the formulation being in a multi-dose or single-dose dosage form; and
   enterally administering one or more doses of the formulation, the formulation including one or more ω-3 fatty acids, one or more curcuminoids, trans-resveratrol, α-glycerylphosphorylcholine ("α-GPC"), and uridine-5'-monophosphate ("UMP").

2. The method of claim 1, wherein the formulation is in the multi-dose dosage form, the multi-dose dosage form selected from a bulk powder, paste, suspension, emulsion, or solution.

3. The method of claim 2, wherein a single dose of the multi-dose dosage form includes about 900 mg of eicosapentaenoic acid and about 600 mg of docosahexaenoic acid for the one or more ω-3 fatty acids, about 500 mg of the one or more curcuminoids including at least curcumin, demethoxycurcumin, and bisdemethoxycurcumin, about 400 mg of the trans-resveratrol, about 300 mg of the α-GPC, and about 200 mg of the UMP.

4. The method of claim 3, wherein the formulation further includes one or more excipients selected from an antiadherent, a binder, a coating, a color, a disintegrant, an emulsifier, a flavor, a glidant, a lubricant, a preservative, a sorbent, a stabilizer, a sweetener, a thickener, and a vehicle.

5. The method of claim 1, wherein the formulation is in the single-dose dosage form, the single-dose dosage form selected from a pre-measured amount of a powder, a paste, a suspension, an emulsion, or a solution; a pill, a tablet, or a capsule; and a pre-cut, orally disintegrating thin film.

6. The method of claim 5, wherein the pill, the tablet, or the capsule includes an effervescent, a chewable, or an orally disintegrating form thereof.

7. The method of claim 5, wherein the single-dose dosage form includes about 900 mg of eicosapentaenoic acid and about 600 mg of docosahexaenoic acid for the one or more ω-3 fatty acids, about 500 mg of the one or more curcuminoids including at least curcumin, demethoxycurcumin, and bisdemethoxycurcumin, about 400 mg of the trans-resveratrol, about 300 mg of the α-GPC, and about 200 mg of the UMP.

8. The method of claim 7, wherein the formulation further includes one or more excipients selected from an antiadherent, a binder, a coating, a color, a disintegrant, an emulsifier, a flavor, a glidant, a lubricant, a preservative, a sorbent, a stabilizer, a sweetener, a thickener, and a vehicle.

9. The method of claim 1, wherein the one or more ω-3 fatty acids promote neurogenesis, neuroplasticity, neurite outgrowth, synaptogenesis, membrane fluidity, or a combination thereof.

10. The method of claim 1, wherein the one or more curcuminoids combat oxidative stress associated with neurons, decrease messenger ribonucleic acid ("mRNA") expression of MCP1, interleukin 1-β, and interleukin-6, ameliorate enhanced hippocampal expression of ionized calcium binding, ameliorate the effects of chronic stress through reduction of cyclooxygenase-2 ("COX-2") levels, increase serum activities of antioxidants including superoxide dismutase ("SOD"), modulate glutathione ("GSH"), catalase, and SOD activity, or a combination thereof.

11. The method of claim 1, wherein the trans-resveratrol reduces proinflammatory cytokine concentration, which is beneficial to reduce interleukin 1-β and tumor necrosis factor, each of which negatively impacts the central nervous system.

12. The method of claim 1, wherein administering the one or more doses of the formulation includes administering one dose of the formulation at least 1 time per day to no more than 4 times per day.

13. A method for improving cognitive function, comprising:
obtaining a formulation for improving cognitive function, the formulation being in a single-dose dosage form selected from a pre-measured amount of a powder, a pre-measured amount of a paste, a pre-measured amount of a suspension, a pre-measured amount of an emulsion, a pre-measured amount of a solution, a pill, a tablet, a capsule, and a pre-cut, orally disintegrating thin film; and
enterally administering at least one dose of the single-dose dosage form once to four times daily, the single-dose dosage form including one or more ω-3 fatty acids including about 900 mg of eicosapentaenoic acid and about 600 mg of docosahexaenoic acid, about 500 mg of one or more curcuminoids including at least curcumin, demethoxycurcumin, and bisdemethoxycurcumin, about 400 mg of trans-resveratrol, about 300 mg of α-glycerylphosphorylcholine ("α-GPC"), and about 200 mg of uridine-5'-monophosphate ("UMP").

14. The method of claim 13, wherein the pill, the tablet, or the capsule includes an effervescent, a chewable, or an orally disintegrating form thereof.

15. The method of claim 13, wherein the formulation further includes one or more excipients selected from an antiadherent, a binder, a coating, a color, a disintegrant, an emulsifier, a flavor, a glidant, a lubricant, a preservative, a sorbent, a stabilizer, a sweetener, a thickener, and a vehicle.

16. A method for improving cognitive function, comprising:
obtaining a formulation for improving cognitive function, the formulation being in a multi-dose dosage form selected from a bulk powder, paste, suspension, emulsion, or solution; and
enterally administering at least one dose of the multi-dose dosage form once to four times daily, the at least one dose of the multi-dose dosage form including one or more ω-3 fatty acids including about 900 mg of eicosapentaenoic acid and about 600 mg of docosahexaenoic acid, about 500 mg of one or more curcuminoids including at least curcumin, demethoxycurcumin, and bisdemethoxycurcumin, about 400 mg of trans-resveratrol, about 300 mg of α-glycerylphosphorylcholine ("α-GPC"), and about 200 mg of uridine-5'-monophosphate ("UMP").

17. The method of claim 16, wherein the formulation further includes one or more excipients selected from an antiadherent, a binder, a coating, a color, a disintegrant, an emulsifier, a flavor, a glidant, a lubricant, a preservative, a sorbent, a stabilizer, a sweetener, a thickener, and a vehicle.

\* \* \* \* \*